US009259255B2

(12) United States Patent
Lewis et al.

(10) Patent No.: US 9,259,255 B2
(45) Date of Patent: Feb. 16, 2016

(54) VARIABLE AXIS LOCKING MECHANISM FOR USE IN ORTHOPEDIC IMPLANTS

(75) Inventors: Derek S. Lewis, Copley, OH (US); Andrew J. Leither, San Diego, CA (US); Rebecca F. DiLiberto, Akron, OH (US)

(73) Assignee: ORTHOHELIX SURGICAL DESIGNS, INC., Medina, OH (US)

( * ) Notice: Subject to any disclaimer, the term of this patent is extended or adjusted under 35 U.S.C. 154(b) by 404 days.

(21) Appl. No.: 12/804,062

(22) Filed: Jul. 13, 2010

(65) Prior Publication Data
US 2011/0015682 A1 Jan. 20, 2011

Related U.S. Application Data

(60) Provisional application No. 61/270,980, filed on Jul. 15, 2009.

(51) Int. Cl.
*A61B 17/88* (2006.01)
*A61B 17/80* (2006.01)
*A61B 17/86* (2006.01)

(52) U.S. Cl.
CPC .............. *A61B 17/88* (2013.01); *A61B 17/8033* (2013.01); *A61B 17/8047* (2013.01); *A61B 17/8052* (2013.01); *A61B 17/8057* (2013.01); *A61B 17/863* (2013.01)

(58) Field of Classification Search
CPC ........... A61B 17/8033; A61B 17/8047; A61B 17/8052; A61B 17/8057; A61B 17/88
USPC ........... 606/280–299, 306, 331; 411/178, 301
See application file for complete search history.

(56) References Cited

U.S. PATENT DOCUMENTS

| 1,956,869 | A | * | 5/1934 | Lipman | 174/152 R |
| 3,001,567 | A | * | 9/1961 | Brill | 411/277 |
| 4,456,010 | A | | 6/1984 | Reimels et al. | |
| 5,104,272 | A | * | 4/1992 | Dupont et al. | 411/339 |
| 5,134,909 | A | | 8/1992 | Sasaki | |
| 5,876,402 | A | | 3/1999 | Errico et al. | |
| 5,954,722 | A | | 9/1999 | Bono | |
| 6,022,350 | A | | 2/2000 | Ganem | |
| 6,030,389 | A | | 2/2000 | Wagner et al. | |
| 6,206,881 | B1 | | 3/2001 | Frigg et al. | |
| 6,331,179 | B1 | | 12/2001 | Freid et al. | |

(Continued)

FOREIGN PATENT DOCUMENTS

WO 2006102110 A1 9/2006
WO 2006103245 A1 10/2006

OTHER PUBLICATIONS

European Search Report dated Jul. 1, 2014.

*Primary Examiner* — Larry E Waggle, Jr.
(74) *Attorney, Agent, or Firm* — Hudak, Shunk & Farine Co. LPA

(57) ABSTRACT

A locking mechanism assembly to allow locking of a fastener in an orthopedic implant having its axis at a variable angle relative to the axis of threaded through opening in the implant. The assembly includes a locking insert, having threads which mates with the threads of the through opening and which includes a smooth opening that forms a torque driving recess and an annular flange. A fixator has a head portion with external threads of a harder material than that which forms the through opening so that the threads of the fixator will deform the insert to lock the fixator in a desired position relative to the plate.

27 Claims, 2 Drawing Sheets

(56) References Cited

U.S. PATENT DOCUMENTS

| | | |
|---|---|---|
| 6,454,769 B2 | 9/2002 | Wagner et al. |
| 6,485,520 B1 | 11/2002 | Hubach et al. |
| 6,623,486 B1 | 9/2003 | Weaver et al. |
| 6,955,677 B2 | 10/2005 | Dahners |
| 6,964,664 B2 | 11/2005 | Freid et al. |
| 7,052,499 B2 | 5/2006 | Steger |
| 7,141,051 B2 | 11/2006 | Janowski et al. |
| 7,175,624 B2 | 2/2007 | Konieczynski et al. |
| 7,201,753 B2 | 4/2007 | Schlapfer et al. |
| 7,229,443 B2 | 6/2007 | Eberlein et al. |
| 2002/0058939 A1 | 5/2002 | Wagner et al. |
| 2004/0073218 A1* | 4/2004 | Dahners .......................... 606/69 |
| 2004/0153073 A1 | 8/2004 | Orbay |
| 2005/0033298 A1 | 2/2005 | Hawkes et al. |
| 2005/0080421 A1 | 4/2005 | Weaver et al. |
| 2005/0143742 A1 | 6/2005 | Porcher |
| 2005/0149040 A1 | 7/2005 | Haines et al. |
| 2005/0277937 A1* | 12/2005 | Leung ................ A61B 17/8057 606/287 |
| 2006/0106398 A1 | 5/2006 | Lauryssen et al. |
| 2006/0116678 A1* | 6/2006 | Impellizzeri ................... 606/69 |
| 2006/0149251 A1* | 7/2006 | Ziolo et al. ...................... 606/69 |
| 2006/0189990 A1 | 8/2006 | Farris et al. |
| 2006/0200148 A1 | 9/2006 | Matthys |
| 2006/0235400 A1 | 10/2006 | Schneider |
| 2007/0083207 A1 | 4/2007 | Ziolo et al. |
| 2007/0088360 A1 | 4/2007 | Orbay et al. |
| 2007/0233116 A1 | 10/2007 | Olerud |
| 2008/0009870 A1 | 1/2008 | Lombardo et al. |
| 2008/0114359 A1 | 5/2008 | Muerner et al. |
| 2008/0119895 A1 | 5/2008 | Manceau |
| 2008/0140130 A1* | 6/2008 | Chan et al. .................. 606/280 |
| 2008/0234677 A1 | 9/2008 | Dahners et al. |
| 2008/0234749 A1 | 9/2008 | Forstein |
| 2009/0018557 A1 | 1/2009 | Pisharodi |
| 2009/0018588 A1 | 1/2009 | Eckhof |
| 2009/0192549 A1 | 7/2009 | Sanders |

* cited by examiner

VARIABLE AXIS LOCKING MECHANISM FOR USE IN ORTHOPEDIC IMPLANTS This is a U.S. patent application of U.S. Provisional Application No. 61/270,980, filed Jul. 15, 2009 for VARIABLE AXIS LOCKING MECHANISM FOR USE IN ORTHOPEDIC IMPLANTS which is hereby fully incorporated by reference.

FIELD OF THE INVENTION

This present invention relates to a mechanism for allowing a screw or peg to be used in an orthopedic implant with the long axis of the screw at a variable angle to the orthopedic implant and subsequently to be locked into a desired orientation. The mechanism comprises an assembly, which is used in a threaded hole in the plate that would otherwise provide for a locking relationship with a locking screw at a fixed angle. Thus the assembly provides the option of either fixed angle locked fixation or locked variable angle fixation using the same plate hole.

BACKGROUND OF THE INVENTION

The present invention provides an advance in the design of an assembly which allows a fixator or fastener, including for example, a screw, or peg, to be inserted through a threaded hole in a stabilizer or implant, such as a plate, anchor or cage, at a variable angle in order to best capture a bone or bone segment with the fixator. The angle of the fixator can subsequently be locked to fix the bone or bone segment relative to the plate, or to fix the plate relative to the bone or bone segment. The invention allows for at least about 10°, and more preferably 15°, of angulation relative to a longitudinal axis of the opening that the fixator is inserted through. The assembly provides the advantage of providing the option to the surgeon of using a locking screw having a threaded head which mates with the threads in the hole to fix the screw at a pre-determined angle, or to use the assembly which comprises a threaded bushing in the hole with a threaded screw at a different desired angle relative to the hole.

There are numerous implant applications that can benefit from a variable angle locking mechanism. Specific examples include use in the small bones, i.e. those bones distal to the elbow and knee and the clavicles, although it is understood, that the mechanism can also be of use in other areas of the body, including the long bones, the pelvis and the spine.

SUMMARY OF THE INVENTION

The assembly of the present invention includes a locking insert that is threaded into, and thus mechanically seated in, the internally threaded opening in an implant. The locking insert has an annular flange or shoulder that surrounds the opening formed about a locking insert axis in the insert and which contacts the implant on the superior surface (relative to the associated bone or bone fragment) in the area surrounding the internally threaded implant opening, and also has a central through opening that is preferably smooth and hexagonal in cross section to allow the insert to be screwed into the plate opening. The locking insert is made from a biocompatible material that can be deformed by the threads of the fixator head, (i.e. a fastener such as a screw or peg,) so that the fixator is inserted through the locking insert and into the adjacent bone to the point where the proximal head threads interact with the internal opening of the locking insert to cause the material to flow and accept the head of the fixator at any angle relative to the locking insert axis (up to)~15° while maintaining a rigid construct. Both the minor diameter and the major diameter of the screw head include a taper to improve the locking within the locking insert. Preferably, the major diameter of the threads taper out at a larger angle than the minor diameter, i.e. by a difference of from about 2° to about 20°, preferably from about 5° to about 15°, and preferably about 8° to about 12° degrees of difference, so that the threads widen toward the proximal end of the screw at a greater rate than the minor diameter of the head.

DETAILED DESCRIPTION OF THE DRAWINGS

Figure 1:
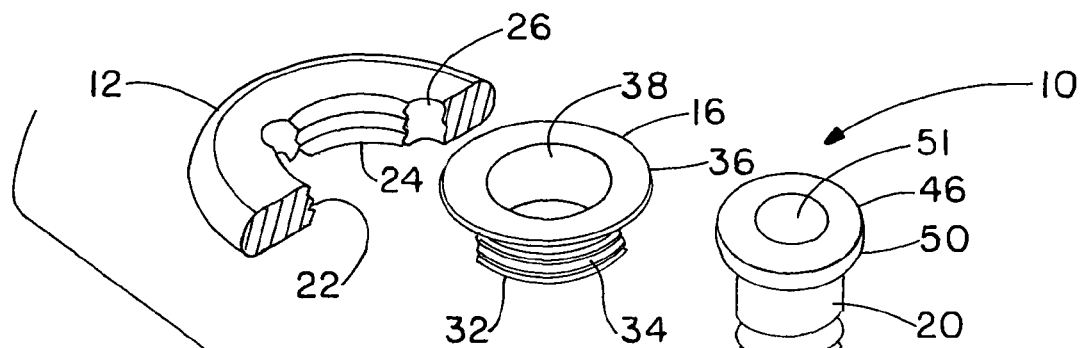
FIG. 1 is an exploded view of a variable locking assembly in accordance with the present invention with the plate illustrated in section.
Figure 3:
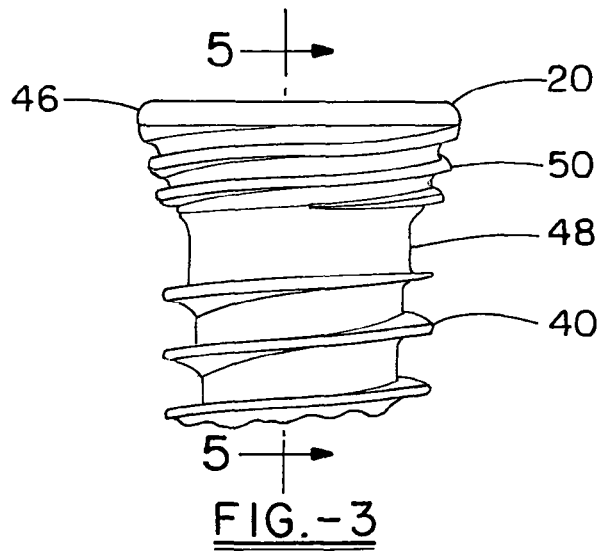
FIG. 3 is a side view of the screw head of FIG. 1.
Figure 4:
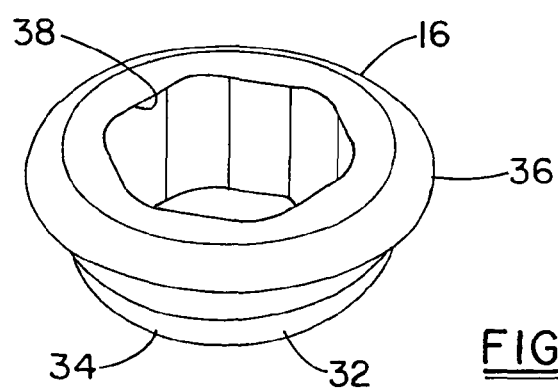
FIG. 4 is a top side view of variable locking insert of FIG. 1.
Figure 5:
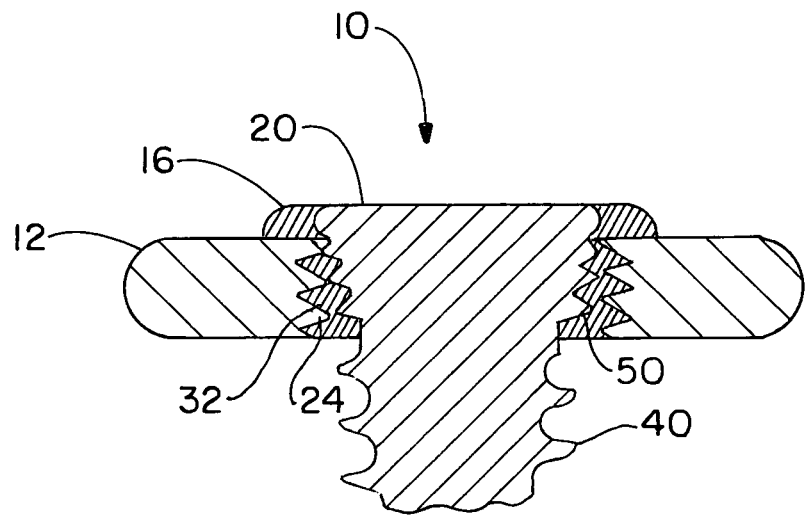
FIG. 5 is a cross section of the variable locking assembly insert of FIG. 2 taken along line 5-5.

FIG. 1 shows an exploded view of a variable axis locking mechanism assembly in accordance with the present invention which are further illustrated in FIGS. 2 through 6. FIG. 5 shows a cross section of the assembly of FIG. 1. The assembly 10 includes an implant member which is shown as a plate 12, a locking insert 16 and a variable locking fixator, which is shown as a screw 20. For the purpose of this description, the plate is shown as part of an annular portion of a plate including a through hole 22 with internal threads 24, and optionally grooves 26 that act as seats for a drill guide having mating cylindrical projections. The plate could have any appropriate shape according to the application with which it is used, such as distal radius plates, calcaneal plates, long bone plates, plates for the clavicles, spinal plates, plates for use in the hand and foot, or any other surgical implant.

The plate generally has a top side, or superior side, i.e. the side which faces away from the bone in use, with a generally constant through thickness to a bottom side, or side that faces toward the bone in use. The plate can be planar, or have another topography, according to the application, although the through hole portion 22 must have a topography that allows the through hole of being capable of receiving the locking insert 16 and the threads 24 of the hole are capable of mating with the external threads 32 of the body 34 of the locking insert or the head of a fastener designed for fixed angle locking. As illustrated in FIG. 4, the locking insert includes an annular flange member 36, which generally forms a shoulder area that seats against the top portion of the plate that surrounds the through hole 22. The locking insert further includes an internal opening 38 that is advantageously smooth and which has a cross-sectional configuration that allows the locking insert to be screwed into the plate hole. Preferably, this is a hexagonal shape having internal edges where the flats join that are smoothed out to better accommodate the screw head. The locking insert is made from a biocompatible material that is softer than the screw so that when the screw head is screwed into the locking insert, the external threads will cause the surface of the internal opening 38 to flow or deform to form threads in the locking insert, causing the screw to lock into position in the locking insert relative to the plate.

Figure 2:
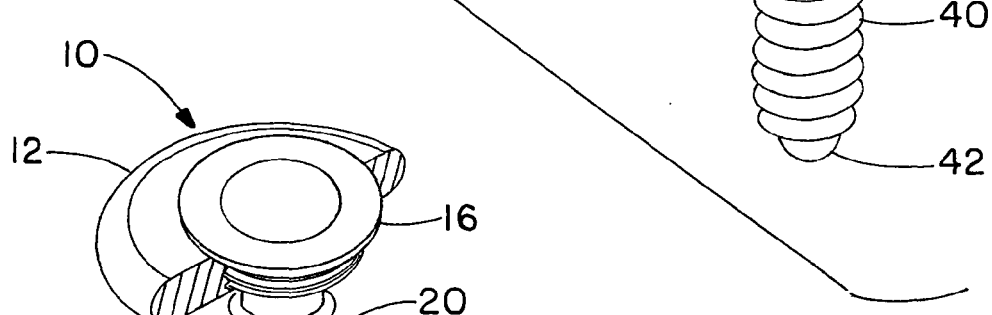
FIG. 2 is a view from the top and the side of the variable locking assembly of the present invention.

FIGS. 1, 2 and 3 show a variable axis locking screw 20 which could also be a variable axis locking peg. The screw includes a portion having a thread 40 for attachment within a bone or bone segment. The screw can include an insertion tip 42 that has a point, or as shown, a blunt tip with optional cutting flutes 44. The screw has a head portion 46 that is joined to the distal threaded portion by an area 48 having threads of a smaller major diameter and also including an area that is free from threads or is cylindrical. The head of the screw includes external threads 50 where the minor diameter and major diameter both taper, but preferably, the major diameter tapers at a larger angle than the minor diameter so that the threads become thicker as they progress toward the top end of the screw. The minor diameter tapers at an angle of from about 20° to about 60°, and preferably from about 30° to about 50° degrees and most preferably about 35° to about 45° while the major diameter tapers at an angle of from about 30° to about 70°, and preferably from about 40° to about 60° degrees and most preferably about 45° to about 55° with an advantageous differential being about 8° to about 12°. The head portion 46 further includes a torque driving recess 52, with an optional bore 80 which retains the screw 54 on the post of a screwdriver.

Figure 6:
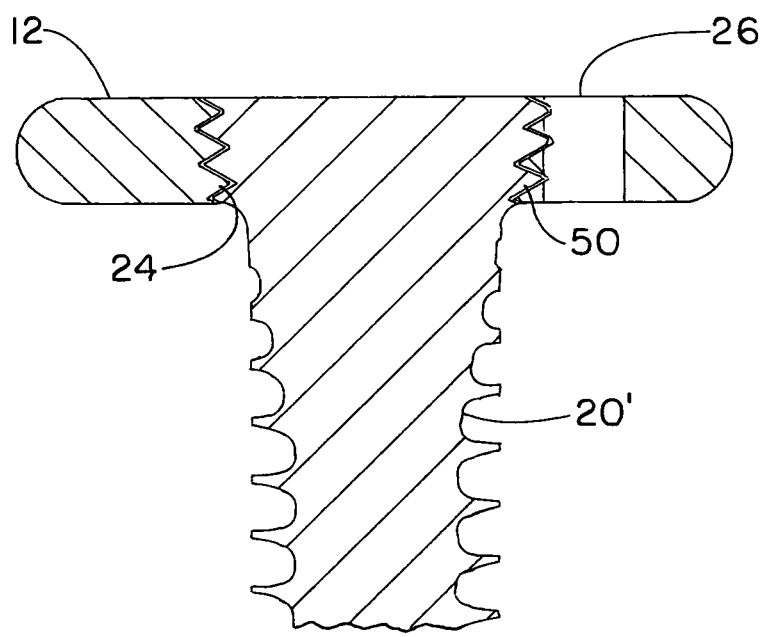
FIG. 6 is a cross section of the plate shown in FIG. 1 with a threaded locking screw.

FIG. 6 illustrates the plate of the present invention accepting a locking screw which has threads on the exterior surface of the head that mate with the internal screws of the through hole in the plate.

While in accordance with the patent statutes the best mode and preferred embodiment have been set forth, the scope of the invention is not limited thereto, but rather by the scope of the attached claims.

What is claimed is:

1. An orthopedic plate system for use in bone, comprising:
   an orthopedic implant including a longitudinal axis, and an external surface surrounding an implant through opening formed about an implant through opening axis and defining an implant internal wall with threads;
   a fixed angle fastener having a head portion having external threads that are capable of mating with the threads of the implant internal wall; and
   a variable angle locking assembly comprising a locking insert having external threads that are capable of mating with the threads of the implant through opening and having a locking insert internal wall defined by a locking insert through opening which forms a torque driving recess about a locking insert through opening axis whereby the locking insert can be screwed into or removed from the through opening of the implant using the torque driving recess, and a variable angle locking fastener having a variable angle fastener longitudinal axis and a portion for attachment in the bone, and a variable angle fastener head having an external threaded portion, the locking insert internal wall comprising a material that will deform relative to a material of the external threads of the head of the variable angle fastener and the external threads of the variable angle fastener head interacting with the locking insert internal wall to cause the material of the locking insert to flow and accept the head of the variable angle fastener so that the variable angle fastener head will seat in the locking insert in a locked relation to the implant whereby the variable angle fastener longitudinal axis may be coaxial with the locking insert through opening axis or may form an angle up to about 15° relative to the locking insert through opening axis.

2. The orthopedic plate system as set forth in claim 1, wherein the implant is a plate and the implant through opening in the plate can selectively accommodate the fixed angle fastener or the locking insert.

3. The orthopedic plate system as set forth in claim 1, wherein the locking insert further includes an annular flange about the locking insert through opening which forms a shoulder having a bottom surface that seats against the external surface of the implant.

4. The orthopedic plate system as set forth in claim 1, wherein the locking insert is made of PEEK and the variable angle locking fastener is made of a metal.

5. The orthopedic plate system as set forth in claim 4, wherein the locking insert through opening has a cross-section that includes flat surfaces which are parallel to the locking insert through opening axis so as to form the torque driving recess.

6. The orthopedic plate system as set forth in claim 5, wherein the cross-section forms a polygon having from 4 to 10 sides which define the flat surfaces.

7. The orthopedic plate system as set forth in claim 6, wherein the polygon has from 5 to 8 sides which define the flat surfaces.

8. The orthopedic plate system as set forth in claim 7, wherein the polygon is a hexagon.

9. The orthopedic plate system as set forth in claim 1, wherein the threaded portion of the variable angle fastener head portion has a minor diameter which has a taper and a major diameter which has a taper.

10. The orthopedic plate system as set forth in claim 9, wherein the taper of the major diameter is larger than the taper of the minor diameter.

11. The orthopedic plate system as set forth in claim 10, wherein the difference in the taper of the major diameter to the minor diameter is from about 5° to about 15°.

12. An orthopedic plate system for use in bone, comprising:
    a plate having a plate through opening with a longitudinal axis and defining a plate internal wall with threads wherein the threads include interruptions formed by grooves which are capable of forming seats for a drill guide and wherein the plate has an external surface which faces away from the bone in use,
    a locking insert assembly comprising a locking insert having external threads that are capable of mating with the threads of the plate through opening and having a locking insert internal wall which defines a locking insert internal through opening that forms a torque driving recess,
    a variable locking screw or peg, having a portion capable of being inserted in the bone, and a head portion having external threads, the locking insert internal wall being of a material that will deform relative to a material of the external threads of the head portion of the screw or peg so that the head portion will seat in the locking insert in a locked relation to the plate; and
    a locking screw or peg, that has a portion capable of being inserted into the bone and having a head portion that includes external threads that are capable of mating with the threads of the through opening of the plate.

13. The orthopedic plate system as set forth in claim 12, wherein the locking insert further includes an annular flange about the locking insert internal through opening which forms a shoulder that mates against the external surface of the plate.

14. The orthopedic plate system as set forth in claim 12, wherein the locking insert is made of PEEK and the variable locking screw or peg is made of a metal.

15. The orthopedic plate system as set forth in claim 14, wherein the locking insert internal through opening is formed about a locking insert internal though opening axis and the locking insert internal through opening has a cross-section that includes flat surfaces which are parallel to the locking insert internal though opening axis.

16. The orthopedic plate system as set forth in claim 15, wherein the cross section is a hexagon.

17. The orthopedic plate system as set forth in claim 12, wherein the external threads of the head portion of the variable locking screw or peg has a minor diameter which has a taper and a major diameter which has a taper, and wherein the taper of the major diameter is larger than the taper of the minor diameter.

18. The orthopedic plate system as set forth in claim 17, wherein the difference in the taper of the major diameter to the minor diameter is from about 5° to about 15°.

19. An orthopedic plate system for use in bone, comprising:
   a plate having an external surface and a plate through opening with a longitudinal axis and defining an internal wall with threads;
   a locking insert assembly comprising an annular shaped insert which has a locking insert internal wall defining a locking insert internal through opening including a torque driving configuration and an external surface including external threads that are capable of mating with the threads of the internal wall of the through opening of the plate and an annular flange about the locking insert internal through opening which forms a shoulder that has a surface that is seated against the external surface of the plate;
   a variable locking screw or peg, having a portion capable of being inserted in the bone, and a head portion having an external threaded portion which defines a major diameter and a minor diameter and the major diameter of the threaded portion tapers out at a larger angle than the minor diameter portion so that threads of the threaded portion widen at a greater rate than the minor diameter of the head, the internal wall of the locking insert being of a material that will deform relative to a material of the external threads of the head portion of the screw or peg so that the head will seat in the locking insert in a locked relation to the plate; and
   a locking screw or peg, that has a portion capable of being inserted into the bone and having a head portion that includes external threads that are capable of mating with the threads of the internal wall of plate the through opening.

20. The orthopedic plate system as set forth in claim 19, wherein the locking insert is made of PEEK and the variable locking screw or peg is made of a metal.

21. The orthopedic plate system as set forth in claim 19, wherein the locking insert internal through opening is formed about a locking insert internal through opening axis and has a cross-section that includes flat surfaces which are parallel to the locking insert internal through opening axis.

22. The orthopedic plate system as set forth in claim 21, wherein the cross section is a hexagon.

23. A method of orthopedic surgery on a bone comprising providing an orthopedic implant system comprising:
   a plate having a through opening with a longitudinal axis and defining a plate internal wall with threads;
   a locking insert assembly comprising an annular shaped insert which has a locking insert internal through opening including a torque driving configuration and a locking insert external surface including external threads that are capable of mating with the threads of the through opening of the plate and an annular flange about the locking insert internal through opening which forms a shoulder that mates against an external surface of the plate and a variable locking screw or peg, having a portion capable of being inserted in the bone, and a head portion having an external threaded portion, the locking insert internal wall being of a material that will deform relative to a material of the external threads of the head portion of the screw or peg so that the head will seat in the locking insert in a locked relation to the plate;
   a locking screw or peg that has a portion capable of being inserted into the bone and having a head portion that includes external threads that are capable of mating with the threads of the through opening of the plate whereby a surgeon is presented with the option of conducting the surgery by attaching the plate using the plate through opening with the plate internal wall with threads with either the locking insert assembly and the variable locking screw or peg or the locking screw or peg; and
   implanting the plate in the orthopedic surgery and placing one of the locking insert assembly, the locking screw, or peg in the plate through opening to fix the plate to the bone.

24. The method of orthopedic surgery as set forth in claim 23 wherein the locking insert is made of PEEK and the variable locking screw or peg is made of a metal.

25. The method of orthopedic surgery as set forth in claim 23, wherein the locking insert_internal through opening has a cross-section that includes flat surfaces.

26. The method of orthopedic surgery as set forth in claim 25, wherein the cross section is a hexagon.

27. The method of orthopedic surgery as set forth in claim 23, wherein the external threaded portion of the head portion of the variable locking screw or peg has a minor diameter which has a taper and a major diameter which has a taper and the taper of the minor diameter is larger than the taper of the major diameter.

* * * * *